United States Patent [19]
Johnson et al.

[11] Patent Number: 5,891,478
[45] Date of Patent: Apr. 6, 1999

[54] COMPOSITION FOR SUSTAINED RELEASE OF HUMAN GROWTH HORMONE

[75] Inventors: OluFunmi Lily Johnson, Cambridge, Mass.; Medha M. Ganmukhi, Wexford, Pa.; Howard Bernstein, Cambridge; Henry Auer, Belmont, both of Mass.; M. Amin Khan, Dowington, Pa.

[73] Assignee: Alkermes Controlled Therapeutics, Inc., Cambridge, Mass.

[21] Appl. No.: 33,193

[22] Filed: Mar. 2, 1998

Related U.S. Application Data

[63] Continuation of Ser. No. 831,604, Apr. 10, 1997, abandoned, which is a continuation of Ser. No. 473,544, Jun. 7, 1995, Pat. No. 5,654,010, which is a continuation-in-part of Ser. No. 984,323, Dec. 2, 1992, abandoned.

[51] Int. Cl.$^6$ .............................. A61F 2/02; A61K 9/14; A61K 9/50; A61K 38/24
[52] U.S. Cl. .......................... 424/502; 424/423; 424/426; 424/489; 424/499; 424/500; 424/501; 514/21; 530/399; 530/839
[58] Field of Search ..................... 424/423, 426, 424/489, 499, 500, 501, 502; 514/21; 530/399, 839

[56] References Cited

U.S. PATENT DOCUMENTS

| | | | |
|---|---|---|---|
| 4,675,189 | 6/1987 | Kent et al. | 424/490 |
| 4,767,628 | 8/1988 | Hutchinson | 424/426 |
| 4,853,218 | 8/1989 | Yim et al. | 424/85.7 |
| 4,891,225 | 1/1990 | Langer et al. | 424/428 |
| 4,897,268 | 1/1990 | Tice et al. | 424/422 |
| 4,906,474 | 3/1990 | Langer et al. | 424/428 |
| 4,962,091 | 10/1990 | Eppstein et al. | 514/2 |
| 4,981,696 | 1/1991 | Loomis et al. | 424/486 |
| 4,985,404 | 1/1991 | Mitchell | 514/2 |
| 5,019,400 | 5/1991 | Gombotz et al. | 424/497 |
| 5,122,367 | 6/1992 | Ron et al. | 424/80 |
| 5,126,147 | 6/1992 | Silvestri et al. | 424/497 |
| 5,176,907 | 1/1993 | Leong | 424/78.08 |
| 5,192,741 | 3/1993 | Orsolini et al. | 514/4 |

FOREIGN PATENT DOCUMENTS

| | | |
|---|---|---|
| 0330180 A1 | 2/1989 | European Pat. Off. . |
| 0537559 | 10/1992 | European Pat. Off. . |
| WO 90/09166 | 8/1990 | WIPO . |
| WO 90/13780 | 11/1990 | WIPO . |
| Wo 91/12882 | 9/1991 | WIPO . |
| WO 92/11844 | 7/1992 | WIPO . |
| WO 93/02712 | 2/1993 | WIPO . |
| WO 93/07861 | 4/1993 | WIPO . |
| WO 93/17668 | 9/1993 | WIPO . |
| WO 93/25221 | 12/1993 | WIPO . |
| WO 94/12158 | 6/1994 | WIPO . |
| WO95/29664 | 9/1995 | WIPO . |
| WO96/073991A1 | 3/1996 | WIPO . |

OTHER PUBLICATIONS

Cunningham, B. C., et al., "Dimerization of Human Growth Hormome by Zinc," *Science*, 253:545–548 (Aug. 2, 1991).

Constantino, H. R., et al., "Solid–Phase Aggregation of Proteins under Pharmaceutically Relevant Conditions," *Journal of Pharmaceutical Sciences*, 83(12):1662–1669 (1994).

Constantino, H. R., et al., "Moisture–Induced Aggregation of Lyophilized Insulin," *Pharmaceutical Research*, 11(1):21–29 (1994).

Constantino, H. R., et al., "Aggregation of a Lyophilized Pharmaceutical Protein, Recombinant Human Albumin: Effect of Moisture and Stabilization by Excipients," *Biotechnology*, 13:493–496 (1995).

Cleland, J. L., et al., "One Month Continuous Release Recombinant Human Growth Hormone–PLGA Formulations," *Proceed. Intern. Symp. Control. Rel. Bioact. Mater.*, 22:149–150 (1995).

Cleland, J. L., et al., "Characterization of Recombinant Human Growth Hormone–PLGA Formulations in Animals," *Proceed. Intern. Symp. Control. Rel. Bioact. Mater.*, 22:143–144 (1995).

*Primary Examiner*—Carlos A. Azpuru
*Attorney, Agent, or Firm*—Hamilton, Brook, Smith & Reynolds, P.C.

[57] ABSTRACT

The method of the invention for producing a composition for the sustained release of biologically active hGH includes dissolving a biocompatible polymer in a polymer solvent to form a polymer solution, dispersing particles of biologically active, metal cation-stabilized hGH in the polymer solution, and then solidifying the polymer to form a polymeric matrix containing a dispersion of said hGH particles.

12 Claims, No Drawings

COMPOSITION FOR SUSTAINED RELEASE OF HUMAN GROWTH HORMONE

RELATED APPLICATIONS

This application is a Continuation of U.S. patent application Ser. No. 08/831,604, filed Apr. 10, 1997, now abandoned, which is a Continuation of U.S. patent application Ser. No. 08/473,544, filed Jun. 7, 1995, now U.S. Pat. No. 5,654,010, which is a Continuation-in-Part of U.S. patent application Ser. No. 07/984,323, filed Dec. 2, 1992, now abandoned. All of the above are incorporated herein by reference in their entirety.

BACKGROUND OF THE INVENTION

Human growth hormone (hGH) is a protein secreted by the pituitary gland and which can be produced by recombinant genetic engineering. hGH will cause growth in all bodily tissues which are capable of growth.

hGH is typically used to treat patients suffering from hypopituitary dwarfism. Currently, aqueous hGH is administered as a subcutaneous bolus three times a week, or once daily, to patients to maintain suitable serum levels of hGH. For patients chronically receiving hGH, the frequent injections result in patient compliance problems.

To resolve the problems associated with repetitive injections of aqueous hGH, attempts have been made to formulate controlled release devices containing higher doses of hGH than a bolus injection, encapsulated within a polymeric matrix wherein the hGH would be released in vivo over a period of about a week or more.

However, these controlled release devices often exhibited high initial bursts of hGH release and minimal hGH release thereafter. Further, due to the high concentration of hGH within these controlled release devices, the hGH molecules have tended to aggregate after several days to form aggregated hGH which is immunogenic in vivo and likely has reduced biological activity.

Therefore, a need exists for a means for sustaining the release of biologically active hGH in vivo without causing an immune system response over the release period of the hGH.

SUMMARY OF THE INVENTION

This invention relates to a composition, and methods of forming and using said composition, for the sustained release of biologically active, stabilized human growth hormone (hGH). The sustained release composition of this invention comprises a polymeric matrix of a biocompatible polymer and particles of biologically active, metal cation-stabilized hGH, wherein said particles are dispersed within the biocompatible polymer.

The method of the invention for forming a composition for the sustained release of hGH, includes dissolving a biocompatible polymer in a polymer solvent to form a polymer solution, dispersing particles of biologically active, stabilized hGH in the polymer solution, and then solidifying the polymer to form a polymeric matrix containing a dispersion of said hGH particles.

The method of using the sustained release composition of the present invention comprises providing a therapeutically effective blood level of biologically active, non-aggregated human growth hormone in a subject for a sustained period by administering to the subject a dose of said sustained release composition.

The advantages of this sustained release formulation for hGH include longer, more consistent in vivo blood levels of hGH, lower initial bursts of hGH, and increased therapeutic benefits by eliminating fluctuations in serum hGH levels. The advantages also include increased patient compliance and acceptance by reducing the required number of injections. The advantages further include the ability to use smaller amounts of hGH compared to bolus injection regimen because serum hGH levels are maintained closer to therapeutical thresholds.

DETAILED DESCRIPTION OF THE INVENTION

The human growth hormone (hGH) used in this invention is biologically active hGH in its molecular (monomeric or non-aggregated) form. Molecular hGH is typically non-immunogenic.

Aggregated hGH may induce an immune response resulting in antibodies formed against hGH. This may compromise the efficacy of long-term hGH therapy. Additionally, aggregated hGH may stimulate an auto-immune response to endogenous hGH.

A sustained release of biologically active, non-aggregated human growth hormone is a release which results in measurable serum levels of biologically active, monomeric hGH over a period longer than that obtained following direct administration of aqueous hGH. It is preferred that a sustained release be a release of hGH for a period of about a week or more, and more preferably for a period of about two weeks or more.

A sustained release of biologically active, non-aggregated hGH from a polymeric matrix can be continuous or non-continuous release with relatively constant or varying rates of release. The continuity of hGH released and level of hGH released can be established by using, inter alia, one or more types of polymer compositions, hGH loadings, and/or selection of excipients to produce the desired effect.

Stabilized (hGH) comprises biologically active, non-aggregated hGH which is complexed with at least one type of multivalent metal cation, having a valency of +2 or more, from a metal cation component. Stabilized hGH in the sustained release composition of the present invention is in particulate form.

Suitable multivalent metal cations include metal cations contained in biocompatible metal cation components. A metal cation component is biocompatible if the cation component is non-toxic to the recipient, in the quantities used, and also presents no significant deleterious or untoward effects on the recipient's body, such as an immunological reaction at the injection site.

Typically, the molar ratio of metal cation component to hGH, for the metal cation stabilizing the hGH, is between about 4:1 to about 100:1 and more typically about 4:1 to about 10:1.

A preferred metal cation used to stabilize hGH is $Zn^{+2}$. In a more preferred embodiment, the molar ratio of metal cation component, containing $Zn^{+2}$ cations, to hGH is about 6:1.

The suitability of a metal cation for stabilizing hGH can be determined by one of ordinary skill in the art by performing a variety of stability indicating techniques such as polyacrylamide gel electrophoresis, isoelectric focusing, reverse phase chromatography, HPLC and potency tests on hGH lyophilized particles containing metal cations to determine the potency of the hGH after lyophilization and for the duration of release from microparticles. In stabilized hGH, the tendency of hGH to aggregate within a microparticle during hydration in vivo and/or to lose biological activity or potency due to hydration or due to the process of forming a sustained release composition, or due to the chemical characteristics of a sustained release composition, is reduced by complexing at least one type of metal cation with hGH prior to contacting the hGH with a polymer solution.

Stabilized hGH is typically stabilized against significant aggregation in vivo over the sustained release period. Significant aggregation is defined as an amount of aggregation resulting in aggregation of about 15% or more of the initial amount of encapsulated hGH monomer. Preferably, aggregation is maintained below about 5% of the initial dose of hGH monomer. More preferably, aggregation is maintained below about 2% of the initial dose.

The hGH in a hGH sustained release composition can also be mixed with other excipients, such as bulking agents or additional stabilizing agents, such as buffers to stabilize the hGH during lyophilization.

Bulking agents typically comprise inert materials. Suitable bulking agents are known to those skilled in the art.

A polymer, or polymeric matrix, suitable for the sustained release composition of the present invention, must be biocompatible. A polymer is biocompatible if the polymer, and any degradation products of the polymer, are non-toxic to the recipient and also present no significant deleterious or untoward effects on the recipient's body, such as an immunological reaction at the injection site.

The polymer of the hGH sustained release composition must also be biodegradable. Biodegradable, as defined herein, means the composition will degrade or erode in vivo to form smaller chemical species. Degradation can result, for example, by enzymatic, chemical and physical processes.

Suitable biocompatible, biodegradable polymers include, for example, poly(lactides), poly(glycolides), poly(lactide-co-glycolides), poly(lactic acid)s, poly(glycolic acid)s, poly (lactic acid-co-glycolic acid)s, polycaprolactone, polycarbonates, polyesteramides, polyanhydrides, poly (amino acids), polyorthoesters, polycyanoacrylates, poly(p-dioxanone), poly(alkylene oxalate)s, biodegradable polyurethanes, blends and copolymers thereof.

Further, the terminal functionalities of the polymer can be modified. For example, polyesters can be blocked, unblocked or a blend of blocked and unblocked polymers. A blocked polymer is as classically defined in the art, specifically having blocked carboxyl end groups. Generally, the blocking group is derived from the initiator of the polymerization and is typically an alkyl group. An unblocked polymer is as classically defined in the art, specifically having free carboxyl end groups.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 6,000 to about 31,000 Daltons.

The amount of hGH, which is contained in a dose of sustained release microparticles, or in an alternate sustained release device, containing biologically active, stabilized hGH particles is a therapeutically or prophylactically effective amount, which can be determined by a person of ordinary skill in the art taking into consideration factors such as body weight, condition to be treated, type of polymer used, and release rate from the polymer.

In one embodiment, an hGH sustained release composition contains from about 0.01% (w/w) to about 50% (w/w) of biologically active, stabilized hGH particles. The amount of such hGH particles used will vary depending upon the desired effect of the hGH, the planned release levels, the times at which hGH should be released, and the time span over which the hGH will be released. A preferred range of hGH particle loading is between about 0.1% (w/w) to about 30% (w/w) hGH particles. A more preferred range of hGH particle loading is between about 0.1% (w/w) to about 20% (w/w) hGH particles. The most preferred loading of the biologically active, stabilized hGH particles is about 15% (w/w).

In another embodiment, a hGH sustained release composition also contains a second metal cation component, which is not contained in the stabilized hGH particles, and which is dispersed within the polymer. The second metal cation component preferably contains the same species of metal cation, as is contained in the stabilized hGH. Alternately, the second metal cation component can contain one or more different species of metal cation.

The second metal cation component acts to modulate the release of the hGH from the polymeric matrix of the sustained release composition, such as by acting as a reservoir of metal cations to further lengthen the period of time over which the hGH is stabilized by a metal cation to enhance the stability of hGH in the composition.

A metal cation component used in modulating release typically contains at least one type of multivalent metal cation. Examples of second metal cation components suitable to modulate hGH release, include, or contain, for instance, $Mg(OH)_2$, $MgCO_3$ (such as $4MgCO_3.Mg(OH)_2.5H_2O$), $ZnCO_3$ (such as $3Zn(OH)_2.2ZnCO_3$), $CaCO_3$, $Zn_3(C_6H_5O_7)_2$, $Mg(OAc)_2$, $MgSO_4$, $Zn(OAc)_2$, $ZnSO_4$, $ZnCl_2$, $MgCl_2$ and $Mg_3(C_6H_5O_7)_2$. A suitable ratio of second metal cation component-to-polymer is between about 1:99 to about 1:2 by weight. The optimum ratio depends upon the polymer and the second metal cation component utilized.

A polymeric matrix containing a dispersed metal cation component to modulate the release of a biologically active agent from the polymeric matrix is further described in co-pending U.S. patent application Ser. No. 08/237,057, filed May 3, 1994, and co-pending PCT Patent Application PCT/US95/05511, the teachings of which are incorporated herein by reference in their entirety.

The hGH sustained release composition of this invention can be formed into many shapes such as a film, a pellet, a cylinder, a disc or a microparticle. A microparticle, as defined herein, comprises a polymeric component having a diameter of less than about one millimeter and having stabilized hGH particles dispersed therein. A microparticle can have a spherical, non-spherical or irregular shape. It is preferred that a microparticle be a microsphere. Typically, the microparticle will be of a size suitable for injection. A preferred size range for microparticles is from about 1 to about 180 microns in diameter.

In the method of this invention for forming a composition for the sustained release of biologically active, non-aggregated hGH, a suitable amount of particles of biologically active, stabilized hGH are dispersed in a polymer solution.

A suitable polymer solution contains between about 1% (w/w) and about 30% (w/w) of a suitable biocompatible polymer, wherein the biocompatible polymer is typically dissolved in a suitable polymer solvent. Preferably, a polymer solution contains about 2% (w/v) to about 20% (w/v) polymer. A polymer solution containing 5% to about 10% (w/w) polymer is most preferred.

A suitable polymer solvent, as defined herein, is solvent in which the polymer is soluble but in which the stabilized hGH particles are substantially insoluble and non-reactive. Examples of suitable polymer solvents include polar organic liquids, such as methylene chloride, chloroform, ethyl acetate and acetone.

To prepare biologically active, stabilized hGH particles, hGH is mixed in a suitable aqueous solvent with at least one suitable metal cation component under pH conditions suitable for forming a complex of metal cation and hGH. Typically, the complexed hGH will be in the form of a cloudy precipitate, which is suspended in the solvent. However, the complexed hGH can also be in solution. In an even more preferred embodiment, hGH is complexed with $Zn^{+2}$.

Suitable pH conditions to form a complex of hGH typically include pH values between about 7.0 and about 7.4. Suitable pH conditions are typically achieved through use of an aqueous buffer, such as sodium bicarbonate, as the solvent.

Suitable solvents are those in which the hGH and the metal cation component are each at least slightly soluble, such as in an aqueous sodium bicarbonate buffer. For aqueous solvents, it is preferred that water used be either deionized water or water-for-injection (WFI).

It is understood that the hGH can be in a solid or a dissolved state, prior to being contacted with the metal cation component. It is also understood that the metal cation component can be in a solid or a dissolved state, prior to being contacted with the hGH. In a preferred embodiment, a buffered aqueous solution of hGH is mixed with an aqueous solution of the metal cation component.

Typically, the complexed hGH will be in the form of a cloudy precipitate, which is suspended in the solvent. However, the complexed hGH can also be in solution. In an even more preferred embodiment, hGH is complexed with $Zn^{+2}$.

The complexed hGH is then dried, such as by lyophilization, to form a particulate of stabilized hGH. The complexed hGH, which is suspended or in solution, can be bulk lyophilized or can be divided into smaller volumes which are then lyophilized. In a preferred embodiment, the complexed hGH suspension is micronized, such as by use of an ultrasonic nozzle, and then lyophilized to form stabilized hGH particles. Acceptable means to lyophilize the complexed hGH mixture include those known in the art.

Preferably, particles of stabilized hGH are between about 1 to about 6 micrometers in diameter. The hGH particles can be fragmented separately, as described in co-pending U.S. patent application Ser. No. 08/006,682, filed Jan. 21, 1993, which describes a process for producing small particles of biologically active agents, which is incorporated herein in its entirety by reference. Alternately, the hGH particles can be fragmented after being added to a polymer solution, such as by means of an ultrasonic probe or ultrasonic nozzle.

In another embodiment, a second metal cation component, which is not contained in the stabilized hGH particles, is also dispersed within the polymer solution.

It is understood that a second metal cation component and stabilized hGH can be dispersed into a polymer solution sequentially, in reverse order, intermittently, separately or through concurrent additions. Alternately, a polymer, a second metal cation component and stabilized hGH and can be mixed into a polymer solvent sequentially, in reverse order, intermittently, separately or through concurrent additions.

The method for forming a composition for modulating the release of a biologically active agent from a biodegradable polymer is further described in co-pending U.S. patent application Ser. No. 08/237,057.

In this method, the polymer solvent is then solidified to form a polymeric matrix containing a dispersion of stabilized hGH particles.

One suitable method for forming an hGH sustained release composition from a polymer solution is the solvent evaporation method described in U.S. Pat. No. 3,737,337, issued to Schnoring et al., U.S. Pat. No. 3,523,906, issued to Vranchen et al., U.S. Pat. No. 3,691,090, issued to Kitajima et al., or U.S. Pat. No. 4,389,330, issued to Tice et al. Solvent evaporation is typically used as a method to form hGH sustained release microparticles.

In the solvent evaporation method, a polymer solution containing a stabilized hGH particle dispersion, is mixed in or agitated with a continuous phase, in which the polymer solvent is partially miscible, to form an emulsion. The continuous phase is usually an aqueous solvent. Emulsifiers are often included in the continuous phase to stabilize the emulsion. The polymer solvent is then evaporated over a period of several hours or more, thereby solidifying the polymer to form a polymeric matrix having a dispersion of stabilized hGH particles contained therein.

A preferred method for forming hGH sustained release microparticles from a polymer solution is described in U.S. Pat. No. 5,019,400, issued to Gombotz et al., and co-pending U.S. patent application Ser. No. 08/443,726, filed May 18, 1995, the teachings of which are incorporated herein by reference in their entirety. This method of microsphere formation, as compared to other methods, such as phase separation, additionally reduces the amount of hGH required to produce a sustained release composition with a specific hGH content.

In this method, the polymer solution, containing the stabilized hGH particle dispersion, is processed to create droplets, wherein at least a significant portion of the droplets contain polymer solution and the stabilized hGH particles. These droplets are then frozen by means suitable to form microparticles. Examples of means for processing the polymer solution dispersion to form droplets include directing the dispersion through an ultrasonic nozzle, pressure nozzle, Rayleigh jet, or by other known means for creating droplets from a solution.

Means suitable for freezing droplets to form microparticles include directing the droplets into or near a liquified gas, such as liquid argon and liquid nitrogen to form frozen microdroplets which are then separated from the liquid gas. The frozen microdroplets are then exposed to a liquid non-solvent, such as ethanol, or ethanol mixed with hexane or pentane.

The solvent in the frozen microdroplets is extracted as a solid and/or liquid into the non-solvent to form stabilized hGH containing microparticles. Mixing ethanol with other non-solvents, such as hexane or pentane, can increase the rate of solvent extraction, above that achieved by ethanol alone, from certain polymers, such as poly(lactide-co-glycolide) polymers.

A wide range of sizes of hGH sustained release microparticles can be made by varying the droplet size, for example, by changing the ultrasonic nozzle diameter. If very large microparticles are desired, the microparticles can be extruded through a syringe directly into the cold liquid. Increasing the viscosity of the polymer solution can also increase microparticle size. The size of the microparticles can be produced by this process, for example microparticles ranging from greater than about 1000 to about 1 micrometers in diameter.

Yet another method of forming an hGH sustained release composition, from a polymer solution, includes film casting, such as in a mold, to form a film or a shape. For instance, after putting the polymer solution containing a dispersion of stabilized hGH particles into a mold, the polymer solvent is then removed by means known in the art, or the temperature of the polymer solution is reduced, until a film or shape, with a consistent dry weight, is obtained. Film casting of a polymer solution, containing a biologically active agent, is further described in co-pending U.S. patent application Ser. No. 08/237,057, the teachings of which are incorporated herein by reference in their entirety.

It is believed that the release of the hGH can occur by two different mechanisms. The hGH can be released by diffusion through aqueous filled channels generated in the polymeric matrix, such as by the dissolution of the hGH or by voids created by the removal of the polymer's solvent during the synthesis of the sustained release composition.

A second mechanism is the release of hGH due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer. Hydrophilic excipients such as salts, carbohydrates and surfactants can also be incorporated to increase hydration and which can alter the rate of erosion of the polymer.

By altering the properties of the polymer, the contributions of diffusion and/or polymer degradation to hGH release can be controlled. For example, increasing the glycolide content of a poly(lactide-co-glycolide) polymer and decreasing the molecular weight of the polymer can enhance the hydrolysis of the polymer and thus, provides an increased hGH release from polymer erosion.

In addition, the rate of polymer hydrolysis is increased in non-neutral pH's. Therefore, an acidic or a basic excipient can be added to the polymer solution, used to form the microsphere, to alter the polymer erosion rate.

The composition of this invention can be administered to a human, or other animal, by injection, implantation (e.g, subcutaneously, intramuscularly, intraperitoneally, intracranially, intravaginally and intradermally), administration to mucosal membranes (e.g., intranasally or by means of a suppository), or in situ delivery (e.g. by enema or aerosol spray) to provide the desired dosage of hGH based on the known parameters for treatment with hGH of the various medical conditions.

The invention will now be further and specifically described by the following examples.

EXAMPLE 1

Formation of $Zn^{+2}$-Stabilized hGH

Human growth hormone (hGH), whose DNA sequence is described in U.S. Pat. No. 4,898,830, issued to Goeddel et al., was used in this Example. The human growth hormone was stabilized by forming insoluble complexes with zinc.

The hGH was dissolved in samples of a 4 mM sodium bicarbonate buffer (pH 7.2) to form hGH solutions with a concentrations between 0.1 and 0.5 mM hGH. A 0.9 mM $Zn^{+2}$ solution was prepared from deionized water and zinc acetate dihydrate and then was added to the hGH solutions to form $Zn^{+2}$-hGH complex. The pH of the $Zn^{+2}$-hGH complex was then adjusted to between 7.0 and 7.4 by adding 1% acetic acid. A cloudy suspended precipitate, comprising $Zn^{+2}$-stabilized hGH formed.

The suspension of $Zn^{+2}$-stabilized hGH was then micronized using an ultrasonic nozzle (Type V1A; Sonics and Materials, Danbury, Conn.) and sprayed into a polypropylene tub (17 cm diameter and 8 cm deep) containing liquid nitrogen to form frozen particles. The polypropylene tub was then placed into a −80° C. freezer until the liquid nitrogen evaporated. The frozen particles, which contained $Zn^{+2}$-stabilized hGH, were then lyophilized to form $Zn^{+2}$-stabilized hGH particles.

EXAMPLE 2

Preparation of PLGA Microspheres Containing Biologically Active, Aggregation-Stabilized hGH Microspheres containing $Zn^{+2}$-stabilized human growth hormone (hGH) were prepared from hydrophilic poly (lactide-co-glycolide) polymer RG502H having free carboxyl end groups (hereinafter "unblocked-PLGA") (50:50 PLGA, 9,300 Daltons; Boehringer Ingelheim Chemicals, Inc.) or a more hydrophobic PLGA polymer having blocked carboxyl end groups (hereinafter "blocked-PLGA") (50:50 PLGA, 10,000 Daltons; Lot #115-56-1, Birmingham Polymers, Inc., Birmingham, Ala.).

The polymer was dissolved in methylene chloride at room temperature. The lyophilized hGH particles were added to the polymer solution and zinc carbonate was also added. The mixture was then sonicated to give a homogeneous suspension. The suspension was atomized through a sonicating nozzle on to a bed of frozen ethanol, overlaid with liquid nitrogen. The vessel containing the microspheres was stored at −80° C. to extract the methylene chloride and then freeze-dried to give a free-flowing powder.

EXAMPLE 3

Analysis of Encapsulated hGH Protein

The integrity of encapsulated hGH was determined by dissolving unhydrated microspheres into methylene chloride and acetone, collecting the protein, freeze-drying and reconstituting in HEPES buffer containing 10 mM EDTA. Appropriate controls were run to ensure that the extraction process did not affect the integrity of the protein.

The integrity of the encapsulated hGH was analyzed by measuring the percent of hGH monomer contained in the hGH after encapsulation through size exclusion chromatography (SEC).

The results of SEC analyses of the hGH integrity of hGH sustained release microspheres are provided below.

| Formulation (polymer; % Zinc Carbonate) | % Monomer (SEC) |
|---|---|
| 31K unblocked; 6% ZnCO3 | 98.6 |
| 31K unblocked; 6% ZnCO3 | 99.2 |
| 31K unblocked; 3% ZnCO3 | 97.7 |
| 31K unblocked; 3% ZnCO3 | 97.8 |
| 31K unblocked; 1% ZnCO3 | 97.6 |
| 31K unblocked; 0% ZnCO3 | 97.8 |

-continued

| Formulation (polymer; % Zinc Carbonate) | % Monomer (SEC) |
| --- | --- |
| 31K unblocked; 0% ZnCO3 | 97.1 |
| 10K blocked; 1% ZnCO3 | 98.2 |
| 10K blocked; 1% ZnCO3 | 98.4 |
| 8K unblocked; 0% ZnCO3 | 98.5 |
| 10K blocked; 1% ZnCO3 | 98.4 |

The results showed that the encapsulation process did not cause aggregation of the protein. The yield percent protein recovered by the extraction procedure (relative to the amount measured by nitrogen content of the microspheres) ranged from about 40 to 98%. The variability is thought to be associated with loss of material during the transfer steps in the procedure and the extraction procedure is being modified to increase protein recovery.

EXAMPLE 4

Determination of the Effect of Zinc Carbonate on In vitro Release Kinetics

The microspheres were formed as described in Example 2 and contained 15% w/w hGH (6:1 Zn:hGH protein complex); 0%, 1%, 6%, 10% or 20% w/w zinc carbonate; and poly(lactide-co-glycolide) polymer.

In vitro release kinetics of the hGH sustained release microsphere formulations containing various concentrations of zinc carbonate were determined by suspending an aliquot (10 mg) of each type of microsphere in different 1.5 ml samples of HEPES buffer (50 mM Hepes, 10 mM KCl, 0.1% NaN3) pH 7.2 and then incubating at 37° C. The amount of protein released was quantitated by sampling the buffer at 1, 3, 7, 10, 14, 21, 28 days after incubation and replenishing with fresh buffer after each sampling.

A curve of cumulative percent released (relative to initial hGH content in the starting mass of microspheres) versus time was plotted. Released protein samples from each time point were assayed for hGH monomer content by size exclusion chromatography.

Zinc carbonate is thought to act as a reservoir of zinc ions so that the formation of the Zn-hGH complex is favored and dissociation into soluble hGH disfavored. Because the aqueous solubility of zinc carbonate is low, the release of zinc ions from the reservoir is slow thus modulating the solubility of the protein.

The analysis found that in the absence of zinc carbonate, the rate of release of the encapsulated hGH was very rapid and all the protein was released in a very short period.

EXAMPLE 5

Assay for hGH After in Vivo Degradation of Blocked-PLGA $Zn^{+2}$-Stabilized hGH Microspheres Microspheres of blocked-PLGA, containing 15% w/w $Zn^{+2}$-stabilized hGH and 0%, 6%, 10% or 20% $ZnCO_3$ were formed by the method of Example 2. Groups of test rats were injected subcutaneously with 50 mg samples of the different hGH microspheres. The rats were sacrificed after 60 days and the skin sample were excised from the injection sites. The excised skin samples were placed in 10% Neutral Buffered Formalin for at least 24 hours. They were then trimmed with a razor blade to remove excess skin and placed in PBS.

Tissue samples were processed by Pathology Associates, Inc. (Frederick, Md.). The skin samples were embedded in glycomethacrylate, sectioned and assayed for the presence of hGH using a HistoScan/LymphoScan Staining Kit (Product #24-408M; Accurate Chemical & Scientific Corp., Westbury, N.Y.) according to the manufacturer's instructions. Tissue samples were scored for the presence or absence of staining which was indicative of the presence or absence of hGH in the sample.

All skin samples, associated with hGH microsphere injections, tested positive for the presence of hGH thus indicating that the blocked-PLGA microspheres still contained hGH after 60 days in vivo.

The method described in Example 2 was used to form microspheres by encapsulating 0% or 15% w/w hGH, in the form of Zn:hGH complex, and also 0%, 1% or 6% w/w $ZnCO_3$ salt, within blocked-PLGA and within unblocked-PLGA.

In vivo degradation of unblocked-PLGA microspheres versus blocked-PLGA microspheres were compared by injecting samples of microspheres into rats and then analyzing the microspheres remaining at the injection site at various times post-injection. Three rats were assayed at each time point for each microsphere sample. On the day of administration of the microspheres, 750 µl of vehicle (3% carboxymethyl cellulose (low viscosity) and 1% Tween-20 in saline) was added to vials containing 50±1 mg of microspheres. Immediately, the vials were shaken vigorously to form a suspension which was then aspirated into a 1.0 cc syringe without a needle.

Rats (Sprague-Dawley males) were anesthetized with a halothane and oxygen mixture. The injection sites (intrascapular region) were shaven and marked with a permanent taboo to provide for the precise excision of skin at the sampling time points. Each rat was injected with an entire vial of microspheres using 18 to 21 gauge needles.

On designated days (days 15, 30, 59 and 90 post-injection for animals receiving blocked-PLGA microspheres, or days 7, 14, 21, 28 and 45 post-injection for animals receiving unblocked-PLGA microspheres) the rats were sacrificed by asphyxiation with $CO_2$ gas and the skin at the injection sites (including microspheres) was excised. Since the microspheres tended to clump at the injection sites, the presence or absence of microspheres was determined visually.

The visual inspections found that the unblocked-PLGA microspheres degraded substantially faster than the blocked-PLGA microspheres, and that the addition of $ZnCO_3$ to the blocked-PLGA substantially slowed polymeric degradation. For example, in the rats injected with unblocked-PLGA microspheres containing 0% hGH and 0% or 1% $ZnCO_3$, no microspheres were visible on day 21. In addition, for rats injected with blocked-PLGA microspheres containing 0% hGH and 0% $ZnCO_3$, a few microspheres were visible on day 60 and none were visible on day 90. Furthermore, for rats injected with blocked-PLGA microspheres containing 0% or 15% hGH and 6% $ZnCO_3$, microspheres were visible on day 90.

EXAMPLE 6

In Vivo Pharmacokinetic Studies of hGH Sustained Release Microspheres in Rats

Studies were conducted in rats to screen various hGH microsphere formulations, determine pharmacokinetic parameters following intravenous (IV), subcutaneous (SC) and SC osmotic pump (Alzet) administration of hGH, and to evaluate serum profiles and in vivo release-rate of various hGh microsphere formulations.

Sprague-Dawley rats were divided into groups of three each, randomized by body weight, and one hGH microsphere formulation was administered to each group. Rats were injected subcutaneously with approximately 7.5 mg of hGH in 50 mg of one type of the different microspheres, suspended in 0.75 ml of an aqueous injection vehicle. The vehicle composition was 3% CMC (low viscosity), 1% Polysorbate 20, in 0.9% NaCl. The microsphere dose delivered was determined indirectly by weighing the residual dose in the injection vial and correcting for residual injection vehicle. The hGH dose was then computed from the protein loading of the microspheres determined by nitrogen analysis.

Blood samples were collected at pre-determined intervals for up to 30 days after injection. Blood samples of 250 µl were collected during the first 24 hours and at least 400 µl at time points after 24 hours. Blood samples were clotted and hGH concentrations in serum were determined using a radio-immuno assay. A radio-immunoassay (RIA) kit from ICN was validated and used to determine the hGH levels in rat serum.

For the determination of pharmacokinetic parameters, hGH in saline was administered to rats by subcutaneous bolus injection, intravenously or delivered via an osmotic pump (Alzet Model 2ML4) which was implanted subcutaneously.

Three groups of rats received single subcutaneous injections of hGH in 0.9% NaCl at 0.5 or 7.5 mg/kg at a dose volume of 1.0 ml/kg and two groups received single intravenous bolus injections of hGH in 0.9% NaCl solution at about 1.0 mg and 5.0 mg of hGH per kg rat with a dose volume of 1.0 ml/kg. For the Alzet pump study, rats were divided into four groups of three rats each, randomized by body weight and dosed with about 20 mg/ml and 40 mg/ml hGH in 0.9% saline solution loaded into pumps (Alzet Model 2002, 200 µl, 14 days release), and with about 4 mg/ml and 12 mg/ml hGH in 0.9% saline solution loaded into pumps (Alzet Model 2ML4, 2 ml, 28 days release). Expected release rates from the pumps correspond to about 2% and 4 to 6% of the ProLease hGH dose (about 15 mg/kg) per day, respectively. The Alzet pumps were implanted subcutaneously in the inter-scapular region after soaking for 1–2 minutes in sterile saline.

The formulations of hGH sustained release microspheres, synthesized as described in Example 2 contained 15% w/w hGH complexed with Zn in a ratio of 6:1 Zn:hGH; 0%, 1%, 3% or 6% w/w zinc carbonate; and 8K unblocked PLGA, 10K blocked PLGA or 31K unblocked PLGA.

To evaluate the various hGH sustained release formulations, Cmax, Cd5 and Cmax/Cd5 were the in vivo indices used, where Cmax is the maximum serum concentration observed, and Cd5 is the serum concentration at day 5 which should approximate the steady state concentration. The results were as follows:

| Formulation | Burst in vitro (%) | % Monomer Day 7 | Cmax (ng/ml) | C day 5 (ng/ml) | Cmax/Css |
|---|---|---|---|---|---|
| 8K PLGA unblocked 0% ZnCO3 | 22.0 ± 0.9 | 99.3* | 323.3 ± 98.6 | 20.4 ± 14.2 | 19.5 ± 10.6 |
| 8K PLGA unblocked 1% ZnCO3 | 16.4 ± 1.6 | 97.3* | 309.0 ± 67.1 | 20.4 ± 14.2 | 39.5 ± 17.7 |
| 8K PLGA | 15.9 ± | 98.7 | 670.5 ± | 9.0 ± | 44.8 ± |

| Formulation | Burst in vitro (%) | % Monomer Day 7 | Cmax (ng/ml) | C day 5 (ng/ml) | Cmax/Css |
|---|---|---|---|---|---|
| unblocked 6% ZnCO3 | 6.9 | | 244.4 | 4.2 | 22.6 |
| 8K PLGA unblocked 3% ZnCO3 | 17.6 ± 2.7 | 99.3 | 358.0 ± 58.9 | 18.8 ± 14.7 | 42.4 ± 6.8 |
| 31K PLGA unblocked 0% ZnCO3 | 12.3 ± 1.1 | 98.2 | 592 ± 318.2 | 4.5 ± 1.5 | 132.5 ± 47.9 |
| 31K PLGA unblocked 1% ZnCO3 | 11.4 ± 1.3 | 98.8 | 432.7 ± 91.6 | 5.1 ± 0.3 | 84.1 ± 14.9 |
| 31K PLGA unblocked 3% ZnCO3 | 7.9 ± 1.9 | 99.4 | 643.6 ± 203.9 | 8.0 ± 2.6 | 93.3 ± 62.0 |
| 31K PLGA unblocked 6% ZnCO3 | 15.8 ± 0.5 | 99.8 | 1691.8 ± 340.0 | 6.6 ± 0.8 | 262.2 ± 83.5 |
| 10K PLGA blocked 1% ZnCO3 | 12.7 ± 0.1 | 99.3 | 615.9 ± 384.3 | 4.5 ± 1.0 | 155.0 ± 126.8 |
| 10K PLGA blocked 3% ZnCO3 | 18.1 ± 3.2 | 99.6 | 1053.2 ± 293.3 | 3.6 ± 0.8 | 291.7 ± 71.1 |
| 10K PLGA blocked 6% ZnCO3 | 9.9 ± 1.4 | 99.0 | 1743.5 ± 428.4 | 4.9 ± 2.7 | 516.1 ± 361.6 |

*Value obtained from duplicate batch of the same formulation.

The results of the screening showed that the two unblocked polymers (8K and 31K) had different in vivo release kinetics compared to the original formulation, which used blocked 10K PLGA and 6% w/w zinc carbonate. Cmax values were generally lower with the unblocked polymer formulations than with the lead formulation which suggested that the in vivo burst may be lower with the unblocked polymer formulations. The burst was defined as the percent of hGH released in the first 24 hours after injection. The in vitro burst values were between 8–22%. The zinc carbonate content of the formulations did not appear to have an effect on the burst or the in vitro release profile.

The serum concentrations between days 4 and 6 were maintained at a fairly constant level above baseline (or the pre-bleed levels) with the unblocked polymer formulations, while serum concentrations with the blocked formulations, at the same time points were close to the baseline levels. The in vitro release data for up to 7 days showed that the released hGH protein was monomeric. Useful data could not be obtained beyond day 6 because of anti-hGH antibody formulation in the rats.

EXAMPLE 7

Rhesus Monkey Pharmacokinetics Study

The objective of this primate study was to evaluate the pharmacokinetic profiles of different hGH sustained release formulations as compared to more traditional methods of administering hGH (e.g., bolus sc injections, daily sc injections and sc injection combined with the use of an osmotic pump) and to determine which hGH sustained release formulation gave the optimal hGH blood concentration profile The formulations for the hGH sustained release microspheres tested were 1) 15% hGH (complexed with Zn at a 6:1 Zn:hGH ratio), 6% w/w zinc carbonate and 10K blocked PLGA; 2) 15% hGH (complexed with Zn at a 6:1 Zn:hGH ratio), 1% w/w zinc carbonate and 8K unblocked PLGA ("RG502H" PLGA polymer); and 3) 15% hGH (complexed with Zn at a 6:1 Zn:hGH ratio), 1% w/w zinc carbonate and 31K unblocked PLGA ("RG503H" PLGA polymer).

There were four monkeys per group and each animal received a single subcutaneous injection into the dorsal cervical region on Day 1. A dose of 160 mg of hGH sustained release microspheres (24 mg of hGH) was administered to each monkey in 1.2 ml of injection vehicle through a 20 gauge needle. The injection vehicle was an aqueous vehicle containing 3% w/v Carboxymethyl Cellulose (sodium salt), 1% v/v Tween 20 (Polysorbate 20) and 0.9% sodium chloride.

The hGH dose was intended to provide measurable hGH serum concentrations for pharmacokinetic analysis. To obtain pharmacokinetic parameters additional study groups of four monkeys each were included, specifically 1) a single subcutaneous injection (24 mg hGH), 2) daily subcutaneous injections (24 mg/28 days=0.86 mg hGH/day), 3) a subcutaneous injection (3.6 mg hGH) combined with an Alzet osmotic pump (20.4 mg hGH) (total dose of 24 mg hGH), and 4) a subcutaneous injection of the injection vehicle as a control (only used 3 monkeys for the vehicle control group).

Blood samples were collected at the following times for hGH, IGF1, IGFBP3 and anti-hGH antibody analyses: -7, -5, -3, pre-dose and, 0.5, 1, 2, 3, 5, 8, 10, 12, 24, 28, 32 and 48 hours, 5, 4, 6, 8, 11, 14, 17, 20, 23, 26, 29, 32, 25, 28, 41, 44, 47, 50, 53, 56 days post-dose.

The concentrations of IGF-1 and hGH in the serum were then measured. An IRMA kit from RADIM (distributed by: Wein Laboratories, P.O. Box 227, Succasunna, N.J.) was used to quantify hGH in monkey serum. The IRMA assay had a limit of quantification in PBS buffer of 0.1 ng/mL and in pooled juvenile rhesus monkey serum of 1.5 ng/mL with a basal GH level of about 4ng/mL.

The IRMA assay was validated over the concentration range 1.5–75 ng/mL for pooled juvenile rhesus monkey serum. The measurement precision and accuracy are within the range of ±10%.

The results showed that the hGH sustained release microspheres were releasing significant, sustained levels of hGH over a one month period while the subcutaneous injections were not able to maintain the same serum levels.

The IGF-1 serum profile showed that serum IGF-1 concentrations were elevated above the baseline values between days 2 and 29 after administering the microparticles. This shows that enough hGH was being released from the hGH sustained release microspheres to cause a pharmacodynamic effect. This also indicates that the hGH released was biologically active which suggest that the encapsulation process had not adversely affected the biopotency of hGH.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

The invention claimed is:

1. A method of forming a composition for the sustained release of human growth hormone from a polymeric matrix comprising the steps of:

a) forming a mixture comprising a biocompatible polymer, particles of metal cation-complexed hGH and a polymer solvent; and b) solidifying the mixture to form a polymeric matrix containing a dispersion of said hGH particles.

2. The method of claim 1 wherein step (a) further comprises the steps of:

(i) forming droplets of the mixture; and (ii) freezing the droplets of step (i), prior to the solidifying of step (b).

3. The method of claim 2 wherein the polymer is solidified by removing the polymer solvent by extraction with a polymer non-solvent.

4. The method of claim 1 wherein the biocompatible polymer is selected from the group consisting of:

poly(lactides), poly(glycolides), poly(lactide-co-glycolides), poly(lactic acid)s, poly(glycolic acid)s, poly(lactic acid-co-glycolic acids)s, polycaprolactones, polycarbonates, polyesteramides, polyanhydrides, poly (amino acids), polyorthoesters, polycyanoacrylates, poly(p-dioxanone)s, poly(alkylene oxalate)s, biodegradable polyurethanes, blends and copolymers thereof.

5. The method of claim 4 wherein the biocompatible polymer is poly(lactide-co-glycolide).

6. The method of claim 1 wherein the metal cation-complexed human growth hormone contains a multivalent metal cation component.

7. The method of claim 6 wherein the multivalent metal cation component is zinc.

8. The method of claim 7 wherein the particles of hGH have a zinc to hGH molar ratio between 4:1 and 100:1.

9. The method of claim 1 further comprising the step of dispersing a second metal cation component in the mixture wherein the second metal cation is not complexed to said human growth hormone.

10. The method of claim 9 wherein the second metal cation component is zinc carbonate.

11. The method of claim 1 wherein the polymeric matrix is in the form of microparticles.

12. The method of claim 1 wherein the final proportion of human growth hormone in the sustained release composition is between 10 and 30 weight percent.

* * * * *